United States Patent [19]

Underhill et al.

[11] 4,284,622

[45] Aug. 18, 1981

[54] ATTRACTANT FOR SUNFLOWER MOTH

[75] Inventors: Edward W. Underhill; Warren F. Steck; Melvin D. Chisholm; Alfred P. Arthur, all of Saskatoon, Canada

[73] Assignee: Canadian Patents & Development Ltd., Ottawa, Canada

[21] Appl. No.: 135,077

[22] Filed: Mar. 28, 1980

[51] Int. Cl.$^2$ ............................................. A01N 17/14
[52] U.S. Cl. ..................................................... 424/84
[58] Field of Search ........................................... 424/84

[56] References Cited
PUBLICATIONS

Underhill et al., Environmental Entomology, 8:740–743, Aug. 1979.
Chemical Abstracts, vol. 83: 75878q (1975), citing Biosci 1975, 30c(3–4) 283–293.

*Primary Examiner*—Donald B. Moyer
*Attorney, Agent, or Firm*—Alan A. Thomson

[57] ABSTRACT

An attractant has been found for the male sunflower moth *Homoeosoma electellum* (Hulst.). Z-9,E-12-tetradecadien-1-ol has been found effective, optionally in the presence of Z-9-tetradecen-1-ol.

11 Claims, No Drawings

ATTRACTANT FOR SUNFLOWER MOTH

FIELD OF THE INVENTION

This invention is directed to an artificial attractant for male moths of *Homoeosoma electellum* (Hulst.), the sunflower moth. Z-9,E-12-tetradecadien-1-ol and certain mixtures thereof have been found effective.

BACKGROUND AND PRIOR ART

The sunflower moth is a major pest of commercially-grown sunflowers in North America particularly in Texas, California and Nebraska. It is migratory in much of the range including the southern fringe of Canada. The female moth deposits its eggs within or among the florets of the sunflower inflorescence and the developing larvae feed on the flower parts and ultimately on mature seeds. If large numbers of moths are present at the time when cultivated sunflowers are at the flowering stage, applications of insecticides may be necessary to avoid severe economic losses. A simple and efficient method of monitoring populations of sunflower moths is desired to enable growers to determine whether spraying will be required. A complicating factor in detecting sunflower moths is their susceptibility to wind migration. In any region the pest may be entirely absent one day and abundant the next, so that intensive and continuous monitoring is required for detection and control. With a chemical attractant, monitoring moth populations, mass trapping of male moths, and widespread disruption of sunflower moth mating (by indiscriminate dissemination), should be possible.

Light traps, frequently used for moth sampling, are non-specific and relatively ineffective for sunflower moths. The use of traps baited with live female sunflower moths necessitates the availability of a laboratory culture of moths as a source of females which would be an expensive and impractical method for widespread monitoring.

Tests have shown that insect traps baited with female *H. electellum* moths have a strong attraction for male moths of this species indicating that a sex pheromone attraction is involved (G. L. Teetes and N. M. Randolph, Journal of Economic Entomology 63: 1358-1359, 1970). No chemical components of the attractant were identified. Other workers have found that a mixture of Z-9,E-12-tetradecadien-1-yl acetate and Z-9,E-12-tetradecadien-1-ol is involved in the pheromone system of the Indian meal moth *Plodia interpunctella* (Hubner). In this pheromone system, the latter compound served to inhibit the response of male almond moths.

SUMMARY OF THE PRESENT INVENTION

Our chemical investigations of the female sex pheromone of *H. electellum* led to the isolation and identification of tetradecan-1-ol (14:OH), Z-9-tetradecen-1-ol (Z9-14:OH) and Z-9,E-12-tetradecadien-1-ol (Z9,E12-14:OH) in the natural pheromone. Preliminary field tests demonstrated male sunflower moths were strongly attracted to traps baited with certain mixtures of Z9-14:OH and Z9,E12-14:OH (E. W. Underhill, A. P. Arthur, M. D. Chisholm, and W. F. Steck, Environmental Entomology 8: 740-743, August 1979). This constitutes the first artificial chemical attractant for male sunflower moths. Z9-14:OH and 14:OH by themselves proved non-attractive.

As a result of further tests, Z-9,E-12-tetradecadien-1-ol, optionally with Z9-tetradecen-1-ol, has been found to strongly attract male sunflower moths to an insect trap or other locus. The Z-9-tetradecen-1-ol seems to serve as a peculiarly effective diluent: it is desirable to increase the volume of, and prolong the action of, small amounts of the attractant. The Z9 compound seems to effectively dilute the vapor of large amounts of the active attractant (high vapor concentrations of the Z-9,E-12-tetradecadien-1-ol have been found to have an inhibitory effect on the male moths).

In accordance with this present invention, a method is provided of attracting male sunflower moths *Homoeosoma electellum*, during the flight period and in the expected locale of such moths, to specific loci or to disseminated attractant; comprising providing at each locus or disseminating, an attractant consisting essentially of Z-9,E-12-tetradecadien-1-ol, in an amount effective to attract such moths.

To dilute the active compound and prolong the action of the attractant, Z-9-tetradecen-1-ol may also be present, preferably in major proportion by wt. The Z9,E12-14:OH and Z9-14:OH can be mixed, suitably in the wt. ratio range 1/100-1/1 respectively.

Thus the invention also includes an attractant composition for male sunflower moths *Homoeosoma electellum* comprising: (a) Z-9,E-12-tetradecadien-1-ol, and (b) Z-9-tetradecen-1-ol.

Field trapping experiments conducted in 1979 compared the efficiency of male sunflower moth captures by traps baited with Z9-14:OH and Z9,E12-14:OH singly and in various combinations with captures by traps baited with live female sunflower moths. The traps used for field testing were commercially available insect traps {Pherocon (trademark) 1-CP, Zoecon Corp., Palo Alto, Calif.} but other traps may be operative. The traps were mounted on posts in grassland areas or adjacent to sunflower fields at a height of 1.5 m, or just above the tops of the sunflowers if they were above 1.5 m. Live female sunflower moths were held within wire mesh cages near the center of the trap, while other traps contained synthetic chemical attractants placed within red rubber septa. The results of the tests (Table 1) showed there was good attraction of sunflower males to traps baited with Z9,E12-14:OH but essentially none were attracted to those containing Z9-14:OH when the two compounds were tested singly. When mixtures of these components were tested, optimal captures occurred in traps containing Z9;E12-14:OH (10 µg)+Z9-14:OH (90 µg) and the number of males captured by this lure was significantly greater than the number caught by female-baited traps. The data indicate the optimum dose of Z9,E12-14:OH is near 10 µg. In another series of field tests it was demonstrated that additions of 14:OH to the optimum two component lure resulted in no significant differences in male moths captured.

Subsequent field trials were conducted to determine whether the addition of Z9-14:OH to Z9,E12-14:OH was required to effect optimum male captures. These tests were carried out near the end of the sunflower flight period and the total number of moths caught was low (Tables 2 and 3); however, the results clearly demonstrated that the additions of Z9-14:OH did not significantly increase the number of males captured in these tests.

In accordance with these test results, it is evident that Z-9,E-12-tetradecadien-1-ol is an effective attractant for male sunflower moths. A suitable range of dissemination rates from the carrier is 1 to 100 nanograms/hour, with an optimal rate of attractant release near 1–5 nanograms/hour. Using commercial 5×9 mm red rubber septa as carriers, from about 1 to 500 micrograms per trap would be a suitable dose range (preferably 1–100, and more preferably 5–20 micrograms). Preliminary tests indicated that excess amounts of attractant destroyed male attraction, i.e. with baits of chemical attractant of 20, 200 and 2000 micrograms, attraction was observed only at the two lower dose levels.

The composition may, if desired, comprise a liquid or solid carrier or substrate. For example, suitable carriers or substrates include vegetable oils, refined mineral oils or fractions thereof, rubbers, plastics, silica, diatomaceous earth and cellulose powder. We have found a rubber carrier very suitable but other modes of dispensing are feasible.

Z-9,E-12-tetradecadien-1-ol, although available from commercial sources, was synthesized and purified in our laboratory by Wittig reaction (R. J. Anderson and C. A. Henrick, J. Am. Chem. Soc. 97: 4327–34, 1975) as follows. Triphenylphosphonium-E3-pentenylide, generated in ether from butyl lithium and E3-pentenyltriphenylphosphonium bromide, was condensed with 9-acetoxynonanal. The purified product, a mixture of E-9,E-12-tetradecadienyl acetate and Z-9,E-12-tetradecadienyl acetate was hydrolyzed with methanolic KOH. Argentation chromatography (N. W. Houx, H. S. Voerman and W. M. F. Jongen, J. Chromatog. 96: 25–32, 1974) gave Z9,E12-14:OH with a purity greater than 99%.

TABLE 1

Effect of component ratio on field captures of male *Homoeosoma electellum*.

| Treatment (μg) | Total number of males captured[1] | |
|---|---|---|
| | Saskatchewan[2] | 3 |
| Z9,E12-14:OH (100) | 18 bcd | 133 d |
| Z9,E12-14:OH (90) + Z9-14:OH (10) | 21 bcd | 134 d |
| Z9,E12-14:OH (80) + Z9-14:OH (20) | 11 cd | 196 bcd |
| Z9,E12-14:OH (60) + Z9-14:OH (40) | 20 bcd | 231 bc |
| Z9,E12-14:OH (40) + Z9-14:OH (60) | 31 bc | 194 cd |
| Z9,E12-14:OH (20) + Z9-14:OH (80) | 36 b | 279 ab |
| Z9,E12-14:OH (10) + Z9-14:OH (90) | 61 a | 345 a |
| Z9-14:OH (100) | 1 d | 12 c |
| Live females | — | 183 cd |
| Blank | 2 d | 10 e |

[1]In each column, common letters follow values not significantly different at the 5% level (Duncan's new multiple range test).
[2]3 × replicated, June 29 to July 6, 1979.
[3]4 × replicated, May 7 to August 6, 1979.

TABLE 2

Effect of addition of Z-9-tetradecen-1-ol on male sunflower moths captured by Z-9-,E-12-tetradecadien-1-ol near Carlyle, Sask.

| Treatment (μg) | Total males captured[1] |
|---|---|
| Z9,E12-14:OH (5) | 24 |
| Z9,E12-14:OH (5) + Z9-14:OH (100) | 22 |

TABLE 2-continued

Effect of addition of Z-9-tetradecen-1-ol on male sunflower moths captured by Z-9-,E-12-tetradecadien-1-ol near Carlyle, Sask.

| Treatment (μg) | Total males captured[1] |
|---|---|
| Z9,E12-14:OH (15) | 5 |
| Z9,E12-14:OH (15) + Z9-14:OH (90) | 8 |
| Z9,E12-14:OH (50) | 3 |
| Z9,E12-14:OH (50) + Z9-14:OH (50) | 18 |

[1]3 × replication July 22 to August 14, 1979. Values are not significantly different at the 5% level (Duncan's new multiple range test).

TABLE 3

Effect of addition of Z-9-tetradecen-1-ol on male sunflower moths captured by Z9,E12-tetradecadien-1-ol near Bushland Texas. August 8 to October 1, 1979.

| Treatment (μg) | Total males captured in:[1] | |
|---|---|---|
| | Grassland area[2] | Sunflower plots[3] |
| Z9,E12-14:OH (1) | 43 ab | 9 a |
| Z9,E12-14:OH (1) + Z9-14:OH (99) | 32 bcd | 6 a |
| Z9,E12-14:OH (10) | 68 a | 10 a |
| Z9,E12-14:OH (10) + Z9-14:OH (90) | 35 bcd | 15 a |
| Z9,E12-14:OH (50) | 16 bcd | 19 a |
| Z9,E12-14:OH (50) + Z9-14:OH (50) | 11 cd | 11 a |
| Z9,E12-14:OH (100) | 21 bcd | 11 a |
| Live females | 4 d | 4 a |

[1]Values followed by different letters are significantly different at the 5% level.
[2]2 × replication.
[3]4 × replication.

We claim:

1. A method of attracting male sunflower moths *Homoeosoma electellum*, during the flight period and in the expected locale of such moths, to specific loci or to disseminated attractant; comprising distributing by one of (a) providing at each locus and (b) disseminating, an attractant consisting essentially of Z-9, E-12-tetradecadien-1-ol, in an amount effective to attract such moths.

2. The method of claim 1 wherein the rate of release of said attractant compound from each locus is of the order of 1–100 ng/h.

3. The method of claim 2 wherein the rate of release is 1–5 ng/h.

4. The method of claim 1 wherein the compound Z-9-tetradecen-1-ol is also present as diluent.

5. The method of claim 4 wherein Z-9-tetradecen-1-ol is present in major proportion by wt.

6. An attractant composition for male sunflower moths *Homoeosoma electellum* consisting essentially of:
   (a) Z-9, E-12-tetradecadien-1-ol, and
   (b) Z-9-tetradecen-1-ol in proportions of (a)/(b) of about 1/100–9/1 by wt.

7. The composition of claim 6 wherein (b) is present in the major proportion by weight.

8. The composition of claim 6 wherein (a) and (b) are in the weight ratio range 1/100–1/1.

9. The composition of claim 6 including a liquid or solid carrier.

10. The composition of claim 6 in combination with a rubber carrier.

11. The composition of claim 6 in dosage unit form adapted to have a rate of release of (a) of the order of from 1 to 5 ng/h.

* * * * *